US005106990A

United States Patent [19]

Ohno et al.

[11] Patent Number: 5,106,990

[45] Date of Patent: Apr. 21, 1992

[54] INDOLENINE DERIVATIVES AS DYES

[75] Inventors: Shigeru Ohno; Yuji Mihara; Keiichi Adachi, all of Minami-ashigara, Japan

[73] Assignee: Fuji Photo Film Co., Ltd., Kanagawa, Japan

[21] Appl. No.: 329,858

[22] Filed: Mar. 28, 1989

Related U.S. Application Data

[60] Division of Ser. No. 147,571, Jan. 19, 1988, Pat. No. 4,839,265, which is a continuation of Ser. No. 894,017, Aug. 7, 1986, abandoned.

[30] Foreign Application Priority Data

Aug. 8, 1985 [JP] Japan ............................... 60-174940

[51] Int. Cl.[5] .................... C07D 209/04; C07D 209/58

[52] U.S. Cl. .................................... 548/427; 548/491; 548/494; 548/509; 548/510; 548/511

[58] Field of Search ............... 548/427, 491, 494, 509, 548/510, 511

[56] References Cited

U.S. PATENT DOCUMENTS 2,895,955 7/1959 Heseltine et al. ................... 548/427

4,839,265 6/1989 Ohno et al. ......................... 430/522

FOREIGN PATENT DOCUMENTS 0707946 1/1980 U.S.S.R. .

*Primary Examiner*—Nicholas S. Rizzo

*Assistant Examiner*—Jyothsna Venkat

*Attorney, Agent, or Firm*—Birch, Stewart, Kolasch & Birch

[57] ABSTRACT

The present invention relates to a dye represented by formula (I):

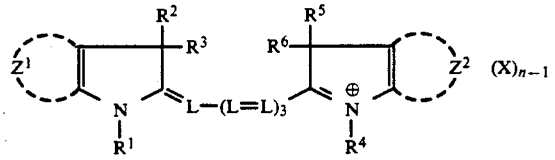

wherein $R^1$, $R^2$, $R^3$, $R^4$, $R^5$ and $R^6$, which may be the same or different, each represents a $C_1$–$C_5$ alkyl group or a $C_1$–$C_5$ alkyl group having a substituent selected from the group consisting of a sulfonic group, carboxyl group and hydroxyl group, and $Z^1$ and $Z^2$ each represents a group of nón-metallic atoms necessary for the formation of a benzo-condensed of naphtho-condensed ring, or a benzo-condensed or naphtho-condensed ring having a substituent selected from the group consisting of a sulfonic group, a carboxyl group, an hydroxyl group, a halogen atom, a cyano group, an amino group and a $C_1$–$C_5$ alkyl group connected to the ring directly or through a divalent connection group, with a proviso that $R^1$, $R^2$, $R^3$, $R^4$, $R^5$, $R^6$, $Z^1$ and $Z^2$ represent those groups which permit the dye molecule to have at least three acid radicals; L represents a methine group of a methine group having a substituent selected from the group consisting of a $C_1$–$C_5$ alkyl group, a $C_1$–$C_5$ alkyl group having a substituent selected from an hydroxyl group, a phenyl group, or a sulfo group, a halogen atom, a phenyl group, a 4-chlorophenyl group, and a $C_1$–$C_2$ alkoxyl group; X represents an anion; and n represents 1 or 2, n being 1 when the dye forms an inner salt.

12 Claims, No Drawings

INDOLENINE DERIVATIVES AS DYES

This application is a divisional of copending application Ser. No. 07/147,571, filed on Jan. 19, 1988, now U.S. Pat. No. 4,839,265 which is a continuation of Ser. No. 06/894,017, filed on Aug. 7, 1986, now abandoned.

BACKGROUND OF THE INVENTION

1. Field of the Invention

The present invention relates to a silver halide photosensitive material having a dyed hydrophilic colloid layer. More particularly, it relates to a silver halide photosensitive material having a hydrophilic colloid layer containing a photochemically inert dye which absorbs light in the infrared region, and is readily discolored during the photographic processing.

2. Description of the Prior Art

In the field of silver halide photosensitive material, it is a common practice to color a photographic emulsion layer or other layers so that they absorb light of specific wavelengths. Where it is necessary to control the spectral energy distribution of light entering a photographic emulsion layer, a colored layer is included at the position farther from the support than the photographic emulsion layer. Such colored layer is called a filter layer. In the case of such a photosensitive material having a plurality of photographic emulsion layers, as in the multi-layer color photosensitive material, the filter layer may be interposed between emulsion layers.

When light passes through a photographic emulsion layer or after light has passed through a photographic emulsion layer, light is sometimes scattered. The scattered light is reflected by the interface between the emulsion layer and the support or by the surface of the photosensitive material opposite to the emulsion layer and enters the photographic emulsion layer again to cause a halo round the image, i.e. halation. In order to prevent halation, a colored layer was included between the photographic emulsion layer and the support or on the surface of the support opposite to the photographic emulsion layer. This colored layer is called antihalation layer. In the case of multi-layer color photosensitive material, an antihalation layer may be interposed between every adjacent two layers.

The coloring of photographic layers was practiced to prevent the lowering of image sharpness due to light scattering in the photographic emulsion layer (the scattering effect is called irradiation).

The layers to be colored are usually made of a hydrophilic colloidal dispersion. Therefore, in many cases they can be colored with a water-soluble dye. The dye should meet the following conditions.

(1) It should have an adequate spectral absorption according to intended uses.

(2) It should be photochemically inert. In other words, it should not afford chemically adverse effects (e.g., decrease of sensitivity, fading of latent image, and fogging) on the performance of the silver halide photographic emulsion layer.

(3) It should be discolored or dissolved and removed during the photographic processing, and should not leave a color harmful on the processed photosensitive material.

Many conventional dyes which absorb visible light or ultraviolet light are known to meet these conditions. They are suitable for the improvement of image on the conventional photosensitive material sensitized for wavelengths shorter than 700 nm. Typical examples in general use are triarylmethane dyes and oxonol dyes.

Recently, there is a demand for the development of a dye for halation prevention and irradiation prevention which absorbs light in the infrared region. Such a dye is useful for a recording material sensitized to near infrared wavelengths, like a photosensitive material to record the output of near infrared laser.

Such a photosensitive material is exposed by scanning an original. An exposure on the silver halide photosensitive material is performed according to the image signals obtained by scanning. Thus a negative image or positive image corresponding to the original is formed. The recording by scanning method employs as a preferred light source a semiconductor laser. It is small, cheap and capable of easy modulation and it has a longer life than He-Ne laser or argon laser. In addition, since it emits in the infrared region, it allows the use of a bright safelight if the photosensitive material is sensitive to infrared. A bright safelight improves the working environment.

So far, there have been no adequate dyes which have an absorption band in the infrared region and meets the abovementioned conditions (1) to (3), and consequently there have been few photosensitive materials which have a high sensitivity in the infrared region and is free from halation and irradiation. Under this situation, the semiconductor laser was not fully utilized in spite of its outstanding properties as mentioned above.

Japanese Patent Application (OPI) No. 100116/1085 discloses that an indoaniline dye can be used for the absorption of infrared. However, it had a disadvantage in practical use that it only absorbed infrared rays of short wavelengths. There is disclosed a polymethine cyanine dye in Japanese Patent Application (OPI) No. 64841/1984. Also, there is disclosed a tricarbocyanine dye in British Patent No. 434,875, U.S. Pat. No. 2,895,955, and Japanese Patent Application (OPI) No. 191032/1984. These dyes have an absorption band in the infrared region but they have a disadvantage of not being photochemically inert.

BRIEF SUMMARY OF THE INVENTION

It is a first object of the present invention to provide a silver halide photosensitive material having a hydrophilic colloid layer colored with a water-soluble dye which does not adversely affect the photographic characteristics of the photographic emulsion and can be discolored upon photographic processing.

It is a second object of the present invention to provide a silver halide photosensitive material which produces good images and is kept in good sensitivity in the infrared region.

It is a third object of the present invention to provide a silver halide photosensitive material which has a high sensitivity to infrared rays and leaves only a slight amount of color after development treatment.

Other and further objects, features, and advantages of the invention will appear more fully from the following description.

DETAILED DESCRIPTION OF THE INVENTION

According to this invention, there is provided a silver halide photosensitive material which comprises a hydrophilic colloidal layer containing at least one kind of the dyes represented by formula (I) below.

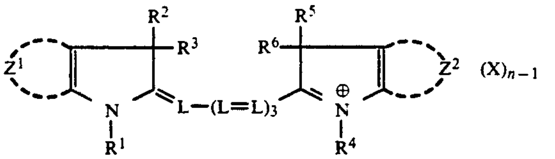

wherein $R^1$, $R^2$, $R^3$, $R^4$, $R^5$, and $R^6$ are the same or different, each represents substituted or unsubstituted alkyl groups; and each of $Z^1$ and $Z^2$ represents a group of non-metallic atoms necessary for the formation of a substituted or unsubstituted benzo-condensed ring or naphtho-condensed ring; provided that among the groups $R^1$, $R^2$, $R^3$, $R^4$, $R^5$, $R^6$, $Z^1$, and $Z^2$ at least 3 groups, and preferably 4 to 6 groups, have an acid substituent group (e.g., sulfonic group and carboxylic group) respectively, and preferably they permit the dye molecule to have 4 to 6 sulfonic groups. In this specification, the sulfonic group represents a sulfo group and a salt thereof, and the carboxylic group represents a carboxyl group and a salt thereof. Examples of the salt include alkali metal salts (e.g., Na and K), ammonium salts, and organic ammonium salts (e.g., triethylamine, tributylamine, and pyridine).

L represents a substituted or unsubstituted methine group; and X represents an anion. Examples of the anion represented by X include halogen ions (such as Cl and Br), p-toluenesulfonic acid ion, and ethyl sulfate ion.

n represents 1 or 2; and it is 1 when the dye forms an inner salt.

The alkyl groups represented by $R^1$, $R^2$, $R^3$, $R^4$, $R^5$ and $R^6$ are preferably lower alkyl groups (e.g., methyl group, ethyl group, n-propyl group, n-butyl group, isopropyl group, and n-pentyl group) having 1 to 5 carbon atoms. They may have a substituent group such as a sulfonic group, carboxyl group or hydroxyl group. More preferably, $R^1$ and $R^4$ are $C_1$-$C_5$ lower alkyl groups having a sulfonic acid group (e.g., 2-sulfoethyl group, 3-sulfopropyl group, and 4-sulfobutyl group).

The benzo-condensed ring or naphtho-condensed ring formed by the group of non-metallic atoms represented by $Z^1$ and $Z^2$ may have a substituent group such as sulfonic acid group, carboxyl group, hydroxyl group, halogen atom (e.g., F, Cl, and Br), cyano group, and substituted amino group (e.g., dimethylamino group, diethylamino group, ethyl-4-sulfobutylamino group, and di(3-sulfopropyl)amino group). Another example of the substituent group is a substituted or unsubstituted alkyl group containing from 1 to 5 carbon atoms connected to the ring directly or through a divalent connecting group. Examples of the alkyl group include methyl group, ethyl group, propyl group, and butyl group; examples of the substituent group introduced thereto include sulfonic acid group, carboxyl group, and hydroxyl group; and examples of the divalent connecting group include —O—, —NHCO—, —NH-$SO_2$—, —NHCOO—, —NHCONH—, —COO—, —CO—, and —$SO_2$—.)

The substituent group on the methine group designated by L includes substituted or unsubstituted lower alkyl groups containing from 1 to 5 carbon atoms (e.g., methyl group, ethyl group, 3-hydroxypropyl group, benzyl group, and 2-sulfoethyl group), halogen atoms (e.g., F, Cl and Br), substituted or unsubstituted aryl groups (e.g., phenyl group and 4-chlorophenyl group), and lower alkoxy groups (e.g., methoxy group and ethoxy group). One substituent group on the methine group designated by L may be connected to another substituent group on the methine group to form a 6-membered ring (e.g., 4,4-dimethylcyclohexene ring) containing three methine groups.

The dye compound represented by formula (I) described above and used in this invention is illustrated by examples in the following; however, the scope of this invention is not limited to them.

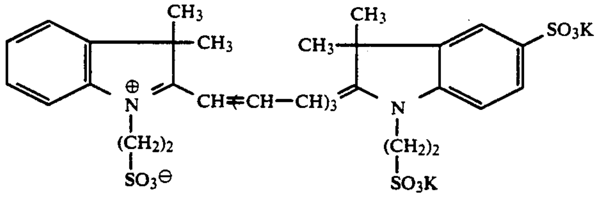

(I-1)

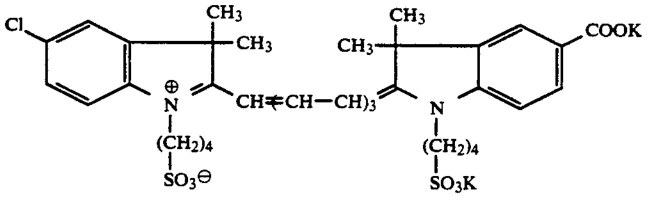

(I-2)

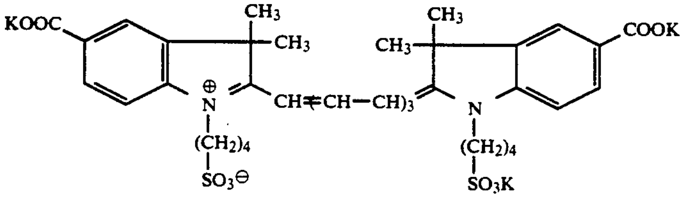

(I-3)

-continued
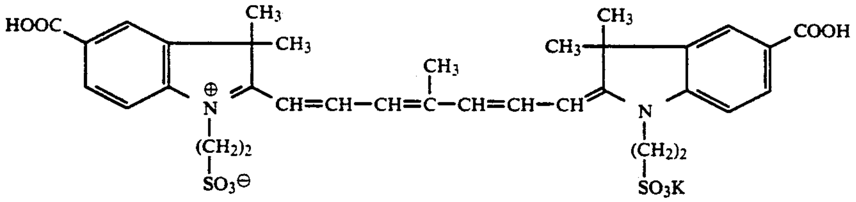
(I-4)
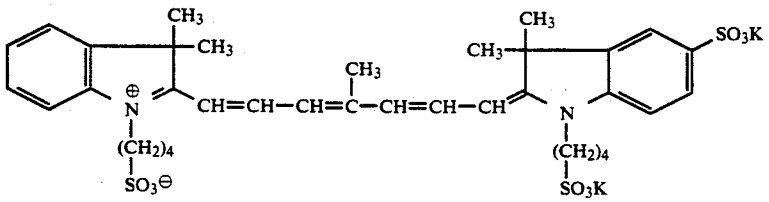
(I-5)
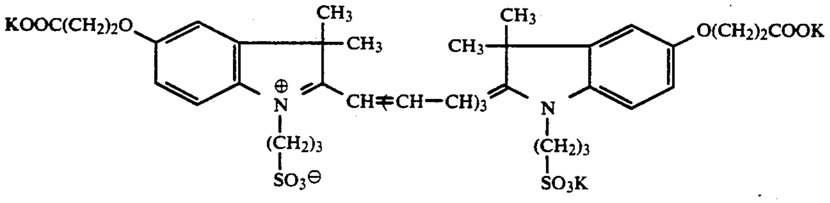
(I-6)
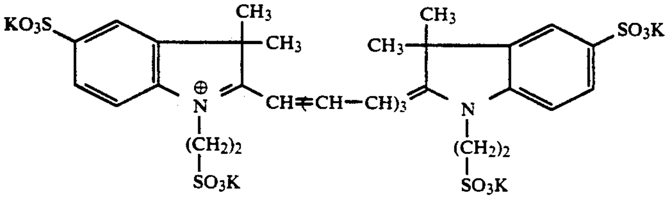
(I-7)
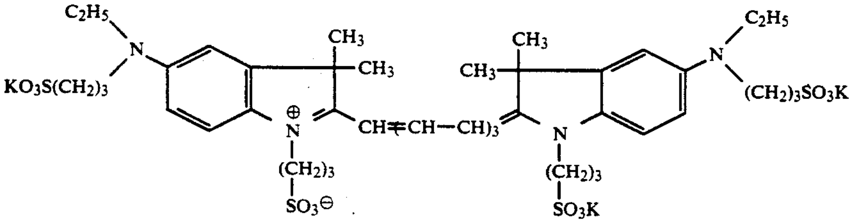
(I-8)
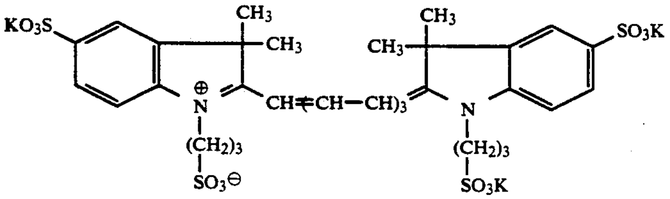
(I-9)
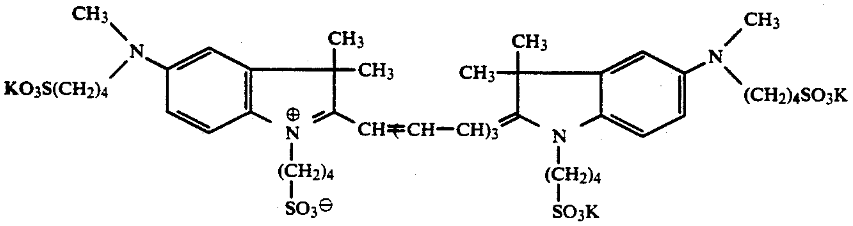
(I-10)

-continued
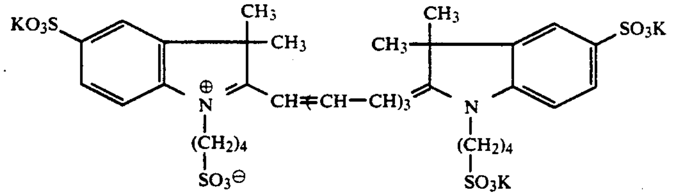
(I-11)
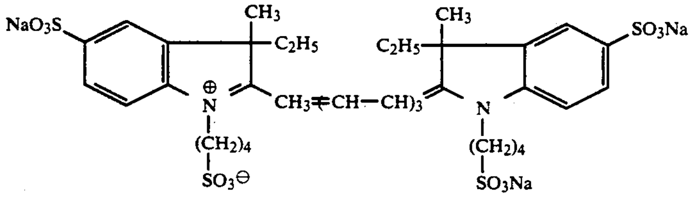
(I-12)
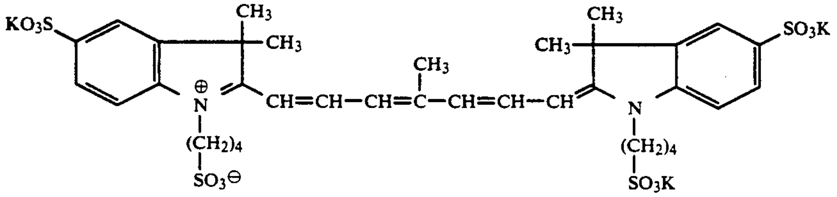
(I-13)
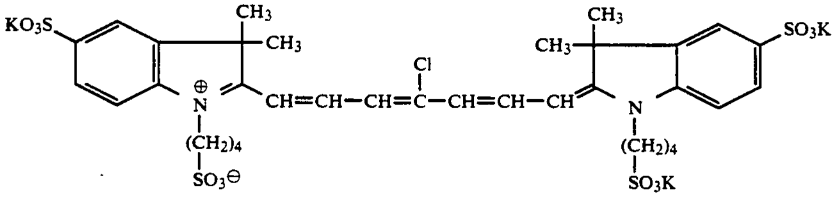
(I-14)
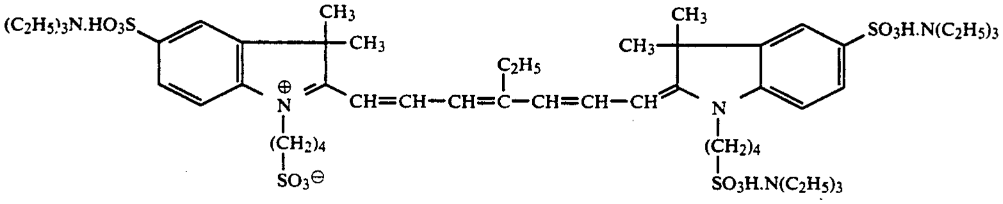
(I-15)
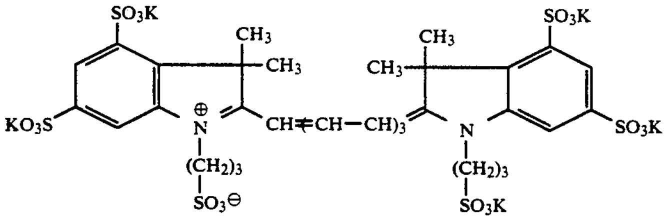
(I-16)
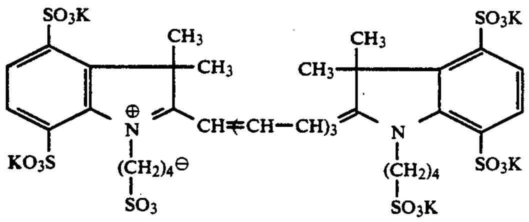
(I-17)
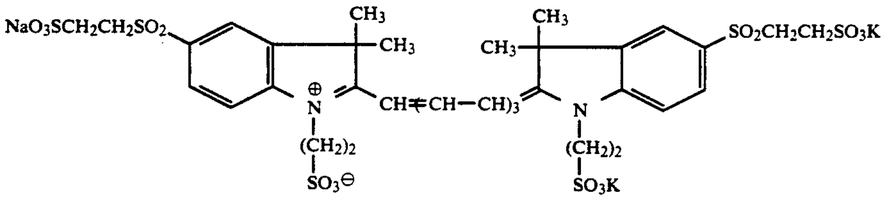
(I-18)

-continued
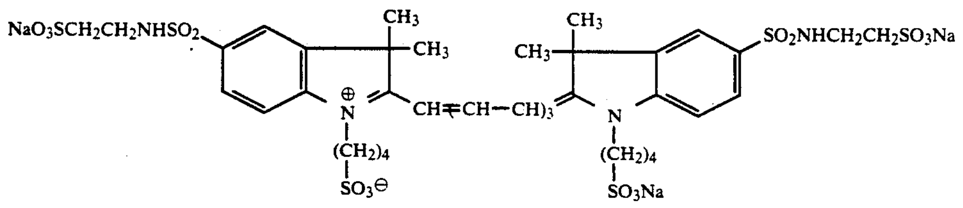
(I-19)
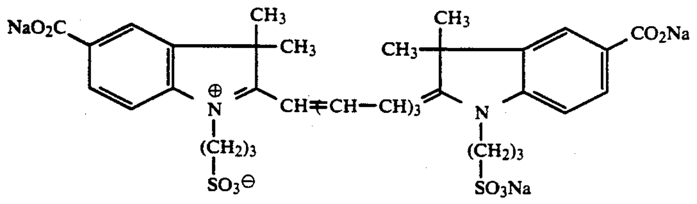
(I-20)
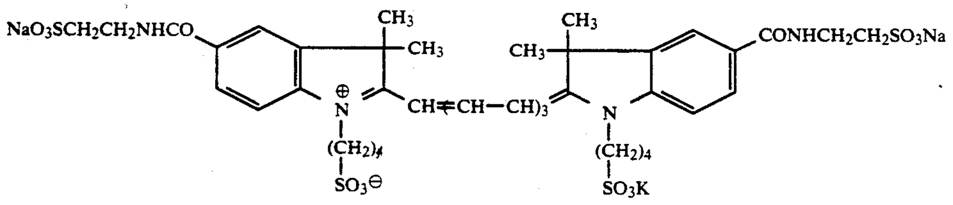
(I-21)
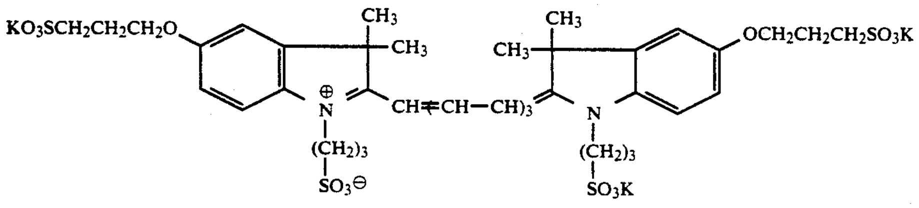
(I-22)
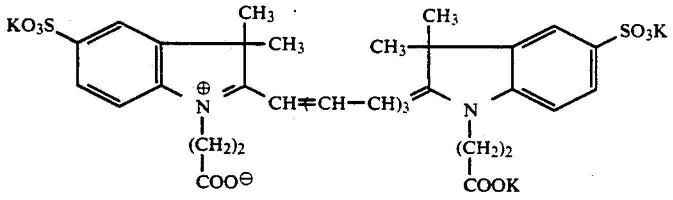
(I-23)
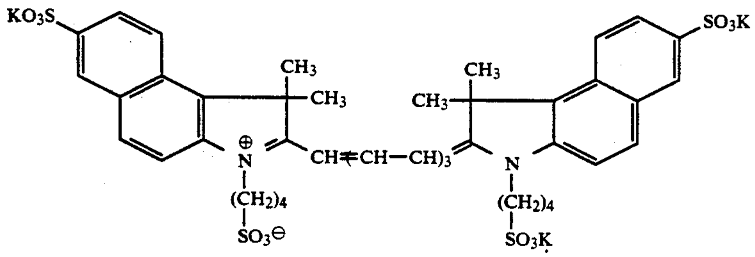
(I-24)
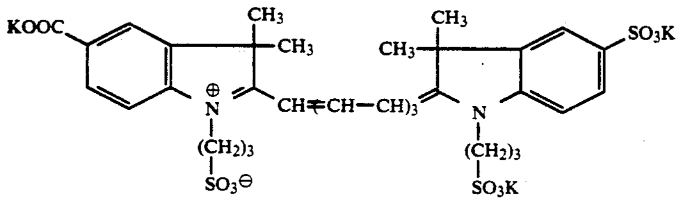
(I-25)

-continued

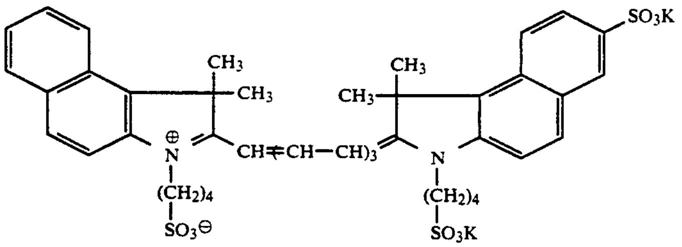

(I-26)

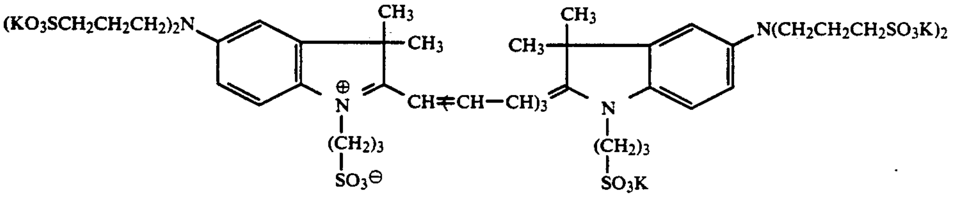

(I-27)

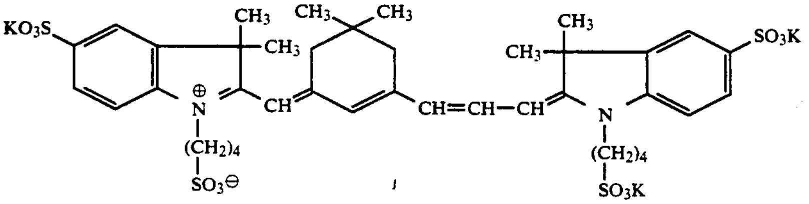

(I-28)

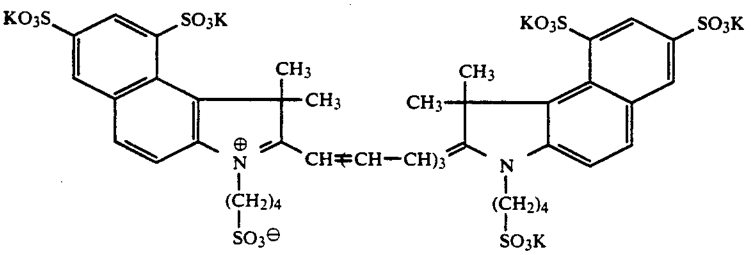

(I-29)

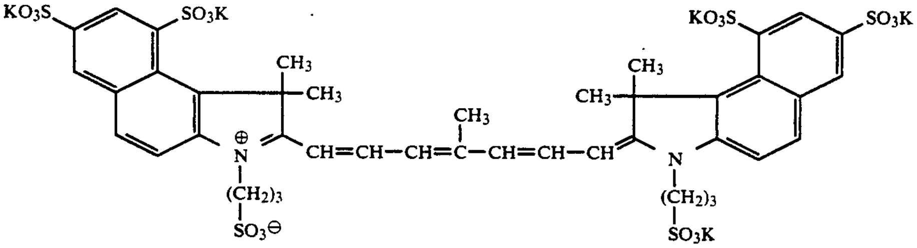

(I-30)

The dye represented by formula (I) has an absorption maximum in the range of wavelengths 730 to 850 nm. It can be synthesized according to the process described in J. Chem. Soc., 189 (1933) and U.S. Pat. No. 2,895,955, or according to the same process as given in the following synthesis examples.

SYNTHESIS EXAMPLE 1 (SYNTHESIS OF DYE I-11)

To 100 ml of methanol solution containing 5.2 g of 1-(4-sulfobutyl)-2,3,3-trimethyl-5-sulfoindolenine were added 7 ml of triethylamine and 2.4 g of glutaconaldehydedianil hydrochloride, and then 2 ml of acetic anhydride was added dropwise. After stirring at room temperature for 2 hours, the reaction liquid was filtered. To the filtrate was added 50 ml of methanol solution containing 2.2 g of potassium acetate, followed by stirring at room temperature for 2 hours. Precipitates were collected by filtration and recrystallized from methanol. Thus there was obtained 1.3 g of dark green crystalline substance, which is dye I-11. Melting point: higher than 260° C. λ max=752 nm in methanol ($\epsilon=19.4\times10^4$).

SYNTHESIS EXAMPLE 2 (SYNTHESIS OF DYE I-13)

To 100 ml of methanaol solution containing 5.2 g of 1-(4-sulfobutyl)-2,3,3-trimethyl-5-sulfoindolenine were added 7 ml of triethylamine and 2.6 g of 3-methylglutacondialdehydedianil hydrochloride, and then 2 ml of acetic anhydride was added dropwise. After stirring at room temperature for 2 hours, the reaction liquid was filtered. To the filtrate was added 50 ml of methanol solution containing 2.2 g of potassium acetate, followed by stirring at room temperature for 2 hours. Precipitates were collected by filtration and recrystallized from methanol. Thus there was obtained 2.1 g of dark green crystalline substance, which is dye I-13. Melting point: higher than 260° C. λ max=772 nm in methanol ($\epsilon=11.9\times10^4$).

The dyes thus produced are dissolved in a proper solvent (e.g., water, alcohol (methanol, ethanol, etc.), methyl cellosolve, and mixtures thereof), and the resulting solution is added to the coating solution for the hydrophilic colloid layer specified in this invention.

Those dyes may be used in combination with one another.

The dye should be used in an amount of $10^{-3}$ g/m$^2$ to 1 g/m$^2$, preferably $10^{-3}$ g/m$^2$ to 0.5 g/m$^2$, depending on the intended use.

The photographic dye represented by the formula (I) above in this invention is effective particularly for the prevention of irradiation. When the dye is used for this purpose, it is usually added to an emulsion layer.

The photographic dye of this invention is also effective for the prevention of halation. When the dye is used for this purpose, it is added to the back side of a support or to an interlayer between the support and an emulsion layer.

The photographic dye of this invention can also be used to allow the photosensitive material to be safe from a safelight. In this case, the dye is added to a layer (e.g., protective layer) on a photographic emulsion layer. If necessary, the dye is used in combination with another dye that absorbs light of different wavelengths.

The photographic dye of this invention is also useful as a filter dye.

The photographic dye of this invention can be introduced into any desired layers constituting the photosensitive material in the usual way. Namely, a solution of the dye of proper concentration is added to an aqueous solution of hydrophilic colloid as a binder of the photographic emulsion layer. The resulting solution is coated on a support or other constituting layers.

The dye of this invention may be added to any of the hydrophilic colloid layers constituting the silver halide photographic material. For example, it may be added to a protective layer, silver halide emulsion layer, antihalation layer, and backing layer.

In the case where the dye of this invention is added to a hydrophilic colloid layer which is substantially non-photosensitive, a proper method should be employed to prevent the dye from diffusing from the non-photosensitive hydrophilic colloid layer to the emulsion layer. According to a preferred method, a silver halide emulsion layer is coated first, and after complete setting of the emulsion layer, a non-photosensitive hydrophilic colloid layer containing the non-diffusing dye is coated on the emulsion layer. In the case where emulsion layers and non-photosensitive hydrophilic colloid layers are coated simultaneously by a multilayer simultaneous coating method, it is preferable to add the non-diffusing dye, alone or in combination with a polymeric mordant, to the non-photosensitive hydrophilic colloid layer.

The photosensitive material of this invention may be used for black and white photosensitive materials as well as color photosensitive materials. Examples of the former include photosensitive materials for printing and infrared photosensitive materials. In this case, it is possible to provide two or more silver halide emulsion layers, although usually one layer is enough. The amount of silver in coating should preferably be in the range of 1 g/m$^2$ to 8 g/m$^2$.

The silver halide employed in this invention may be any of silver chloride, silver bromide, silver iodide, silver chlorobromide, silver chloroiodide, silver iodobromide, and silver chloroiodobromide.

In the case of black and white photosensitive material, the silver halide should have an average grain size of 1.0 μm or less, preferably of 0.7 μm or less.

The silver halide grains in the photographic emulsion may be regular grains having the regular crystal structure such as cube, octahedron, and tetradecahedron, or the spherical or irregular crystal structure, or those having crystal defects such as twin plane, or the combination thereof.

The emulsion in this invention may contain monodisperse silver halide grains of narrow grain size distribution or polydisperse silver halide grains of broad grain size distribution.

The silver halide photographic emulsion used in this invention can be prepared by a known process such as the one described in Research Disclosure (RD), No. 17643 (December 1978), p. 22–23, "I. Emulsion preparation and types" and RD, No. 18716 (November 1979), p. 643.

The photographic emulsion used in this invention can be prepared according to the processes described in "Chimie et Physique Photographique" by P. Glafkides (Paul Montel, 1967), "Photographic Emulsion Chemistry" by G. F. Duffin (Focal Press, 1966), and "Making and Coating Photographic Emulsion" by V. L. Zelikman (Focal Press, 1964).

When the silver halide grains used in this invention are produced, the growth of grains may be controlled by adding a silver halide solvent such as ammonia, potassium thiocyanate, ammonium thiocyanate and thioether compounds as disclosed in U.S. Pat. Nos. 3,271,157, 3,574,628, 3,704,130, 4,297,439, and 4,276,374, thion compounds as disclosed in Japanese Patent Application (OPI) Nos. 144319/1978, 82408/1978, and 77,737/1980, and amine compounds as disclosed in Japanese Patent Application (OPI) No. 100,717/1979).

In this invention, it is possible to use a water-soluble rhodium salt or water-soluble iridium salt.

In this invention, the reaction of the soluble silver salt with the soluble halide may be accomplished by the single-jet method or the double-jet method or a combination thereof. The so-called reversal mixing process may also be employed, in which case the grains are formed in the presence of excess silver ions. The so-called controlled double-jet method may also be used, in which case the pAg is kept constant in the liquid phase where the silver halide is formed. This method provides a silver halide emulsion containing regular crystals of uniform size.

The silver halide emulsion used in this invention may be chemically sensitized. Chemical sensitization is accomplished by means of the ordinary sulfur sensitization, reduction sensitization, or noble metal sensitization, or a combination thereof.

Examples of chemical sensitizers include sulfur sensitizers such as allyl thiocarbamide, thiourea, thiosulfate, thioether, and cystine; noble metal sensitizers such as potassium chloroaurate, aurous thiosulfate, and potassium chloropalladate; and reduction sensitizers such as tin chloride, phenylhydrazine, and reductone.

The photographic emulsion used in this invention may undergo spectral sensitization, according to need, by the aid of a known spectral sensitizing dye such as the one described in Research Disclosure Vol. 176, No. 17643, Section IV (December 1978).

The silver halide photosensitive material of this invention exhibits its best performance when it is made infrared-sensitive so that the silver halide emulsion is most sensitive to the light of wavelengths of 750 nm or more. The infrared sensitizing dye is not specifically limited; however, from the standpoint of sensitizing performance and safety it is preferable to use a tricarbocyanine dye and/or 4-quinoline nucleus-containing dicarbocyanine dye. The silver halide emulsion which has undergone infrared spectral sensitization sometimes is deteriorated in stability. To prevent this trouble, the emulsion may be incorporated with a water-soluble bromide or iodide.

Among the tricarbocyanine dyes used for infrared sensitization, those represented by the following formula (IIa) or (IIb) are particularly effective.

Formula (IIa):

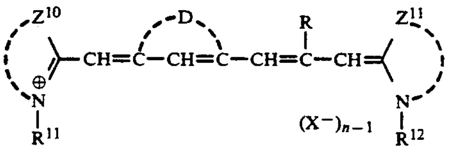

Formula (IIb):

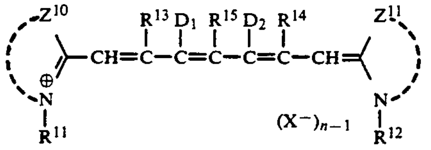

wherein $R^{11}$ and $R^{12}$ are the same or different each other, each denoting an alkyl group (preferably alkyl group having 1 to 8 carbon atoms such as methyl group, ethyl group, propyl group, butyl group, pentyl group, and heptyl group), or a substituted alkyl group containing 6 or less carbon atoms in the alkyl portion and having a substituent group such as a carboxyl group, sulfo group, cyano group, halogen atom (e.g., fluorine atom, chlorine atom, and bromine atom), hydroxyl group, alkoxycarbonyl group (having 8 or less carbon atoms, e.g., methoxycarbonyl group, ethoxycarbonyl group, and benzyloxycarbonyl group), alkoxy group (having 7 or less carbon atoms, e.g., methoxy group, propoxy group, butoxy group, and benzyloxy group), aryloxy group (e.g., phenoxy group and p-tolyloxy group), acyloxy group (having 3 or less carbon atoms, e.g., acetyloxy group and propionyloxy group), acyl group (having 8 or less carbon atoms, e.g., acetyl group, propionyl group, benzoyl group, and mesyl group), carbamoyl group (carbamoyl group, N,N-dimethylcarbamoyl group, morpholinocarbamoyl group, and piperidinocarbamoyl group), sulfamoyl group (e.g., sulfamoyl group, N,N-dimethylsulfamoyl group, and morpholinosulfonyl group), or aryl group (e.g., phenyl group, p-hydroxyphenyl group, p-carboxyphenyl group, p-sulfophenyl group, and α-naphthyl group)). The alkyl group may have two or more substituent groups.

R represents a hydrogen atom, methyl group, methoxy group, or ethoxy group.

$R^{13}$ and $R^{14}$ each independently represents a hydrogen atom, low alkyl group (e.g., methyl group, ethyl group, and propyl group), lower alkoxy group (e.g., methoxy group, ethoxy group, propoxy group, and butoxy group), phenyl group, and benzyl group.

$R^{15}$ represents a hydrogen atom, lower alkyl group (e.g., methyl group, ethyl group, and propyl group), lower alkoxy group (e.g., methoxy group, ethoxy group, propoxy group, and butoxy group), phenyl group, benzyl group, and

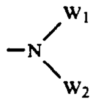

(where $W_1$ and $W_2$ each represents a substituted or unsubstituted alkyl group (the alkyl moiety is a group having 1 to 18 carton atoms and preferably 1 to 4 carbon atoms, e.g., methyl group, ethyl group, propyl group, butyl group, benzyl group, and phenylethyl group), and aryl group (e.g., phenyl group, naphthyl group, tolyl group, and p-chlorophenyl group); and $W_1$ and $W_2$ may be connected to each other to form a 5- or 6-membered nitrogen-containing heterocyclic ring.)

D represents a group of atoms necessary for the completion of a divalent ethylenic bond such as ethylene or triethylene. This ethylenic bond may be further substituted by one, two, or more groups such as alkyl groups having 1 to 4 carbon atoms (e.g., methyl group, ethyl group, propyl group, isopropyl group, and butyl group), halogen atoms (e.g., chlorine atoms and bromine atoms), and alkoxy groups having 1 to 4 carbon atoms (e.g., methoxy group, ethoxy group, propoxy group, isopropoxy group, and butoxy group).

$D_1$ and $D_2$ each represents a hydrogen atom. $D_1$ and $D_2$ may jointly form a divalent ethylenic bond as defined above for D.

$D^{10}$ and $D_{11}$ each represents a group of non-metallic atoms necessary for the completion of a 5- or 6-membered nitrogen-containing heterocyclic ring.

Examples of the heterocyclic ring include thiazole nucleus (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 5-iodobenzothiazole, 5-phenylbenzothiazole, 5-methoxybenzothiazole, 6-methoxybenzothiazole, 5-ethoxybenzothiazole, 5-carboxybenzothiazole, 5-ethoxycarbonylbenzothiazole, 5-phenethylbenzothiazole, 5-fluorobenzothiazole, 5-trifluorobenzothiazole, 5,6-dimethylbenzothiazole, 5-hydroxy-6-methylbenzothiazole, tetrahydrobenzothiazole, 4-phenylbenzothiazole, naphtho[2,1-d]thiazole, naphtho[1,2-d]thiazole, naphtho[2,3-d]thiazole, 5-methoxynaphtho[1,2-d]thiazole, 7-ethoxynaphtho[2,1-d]thiazole, 8-methoxynaphtho[2,1-d]thiazole, and 5-methoxynaphtho[2,3-d]thiazole), selenazole nucleus (e.g., benzoselenazole, 5-chloroselenazole, 5-methoxybenzoselenazole, 5-methylbenzoselenazole, 5-hydroxybenzoselenazole, naphtho[2,1-d]selenazole, and naphtho[1,2-d]selenazole), oxazole nucleus (e.g., benzoxazole, 5-chlorobenzoxazole, 5-methylbenzoxazole, 5-bromobenzoxazole, 5-fluorobenzoxazole, 5-phenylbenzoxazole, 5-methoxybenzoxazole, 5-trifluorobenzoxazole, 5-hydroxybenzoxazole, 5-carboxybenzoxazole, 6-methylbenzoxazole, 6-chlorobenzoxazole, 6-methoxybenzoxazole, 4,6-dimethylbenzoxazole, 5-ethoxybenzoxazole, naphtho[2,1-d]oxazole, naphtho[1,2-d]oxazole, and naphtho[2,3-d]oxazole), quinoline nucleus (e.g., 2-quinoline, 3-methyl-2-quinoline, 5-ethyl-2-quinoline, 6-methyl-2-quinoline, 8-fluoro-2-quinoline, 6-methoxy-2-quinoline, 6-hydroxy-2-quinoline, 8-chloro-2-quinoline, and 8-fluoro-4-quinoline), 3,3-dialkylindolenine nucleus (e.g., 3,3-dimethylindolenine, 3,3-diethylindolenine, 3,3-dimethyl-5-cyanoindolenine, 3,3-dimethyl-5-cyanoindolenine, 3,3-dimethyl-5-methoxyindolenine, 3,3-dimethyl-5-methylindolenine, and 3,3-dimethyl-5-chloroindolenine), imidazole nucleus (e.g., 1-methylbenzimidazole, 1-ethylbenzimidazole, 1-methyl-5-chlorobenzimidazole, 1-methyl-5,6-dichlorobenzimidazole, 1-ethyl-5,6-dichlorobenzimidazole, 1-alkyl-5-methyoxybenzimidazole, 1-methyl-5-cyanobenzimidazole, 1-ethyl-5-cyanobenzimidazole, 1-methyl-5-fluorobenzimidazole, 1-ethyl-5-fluorobenzimidazole, 1-phenyl-5,6-dichlorobenzimidazole, 1-allyl-5,6-dichlorobenzimidazole, 1-allyl-5-chlorobenzimidazole, 1-phenylbenzimidazole, 1-phenyl-5-chlorobenzimidazole, 1-methyl-5-trifluoromethylbenzimidazole, 1-ethyl-5-trifluoromethylbenzimidazole, and 1-ethyl-naphtho[1,2-d]imidazole), pyridine nucleus (e.g., pyridine, 5-methyl-2-pyridine, and 3-methyl-4-pyridine).

Among those listed above, the thiazole nucleus and oxazole nucleus are preferable, and the benzothiazole nucleus, naphthothiazole nucleus, naphthoxazole nucleus, and benzoxazole nucleus are more preferable.

X represents an anion.

n represents 1 or 2.

Among the quinoline nucleus-containing dicarbocyanine dyes used in this invention, those represented by the following formula (IIc) are particularly preferable.

Formula (IIc):

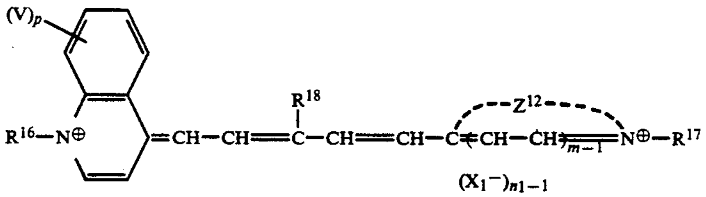

wherein $R^{16}$ and $R^{17}$ have the same meaning as $R^{11}$ and $R^{12}$, respectively.

$R^{18}$ has the same meaning as $R^{13}$. Preferably, $R^{18}$ is a lower alkyl group or benzyl group.)

V represents a hydrogen atom, lower alkyl group (e.g., methyl group, ethyl group, and propyl group), alkoxy group (e.g., methoxy group, ethoxy group, and butoxy group), halogen atom (e.g., fluorine atom and chlorine atom), and substituted alkyl group (e.g., trifluoromethyl group and carboxymethyl group).

$Z^{12}$ has the same meaning as $Z^{10}$ and $Z^{11}$.

$X_1$ has the same meaning as X.

m, $n_1$, and p each denotes 1 or 2.

Examples of the sensitizing dyes used in this invention are shown in the following, but the scope of this invention should not be construed as being limited thereto.

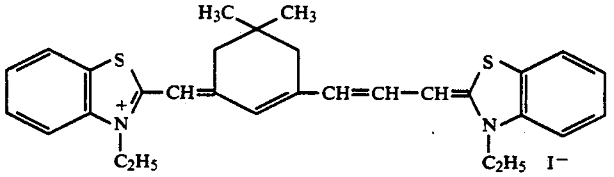

(II-1)

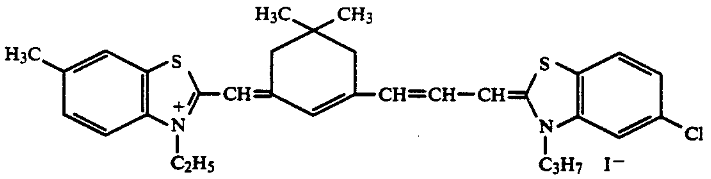

(II-2)

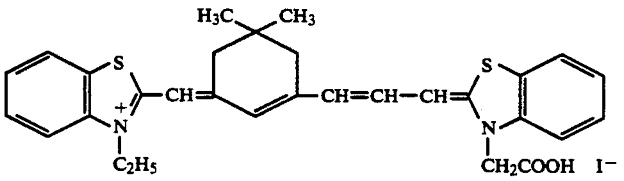

(II-3)

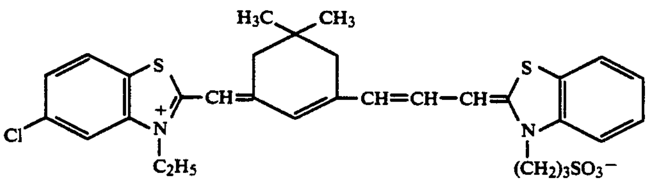

(II-4)

-continued
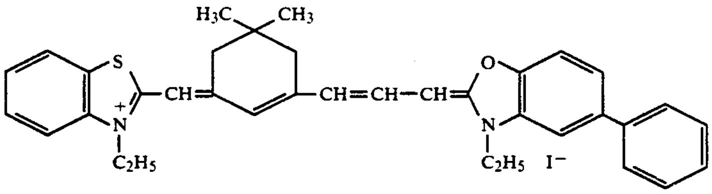
(II-5)
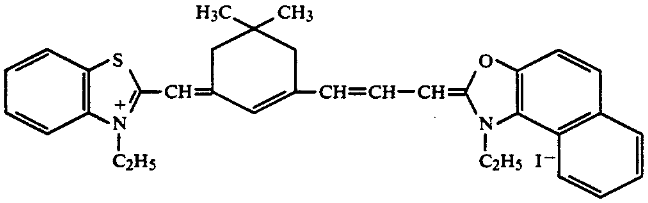
(II-6)
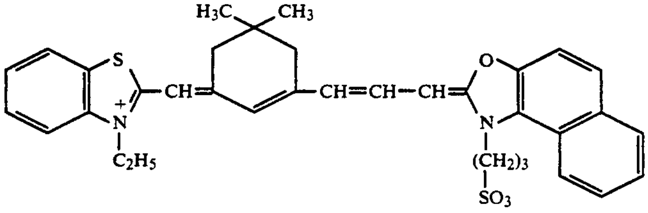
(II-7)
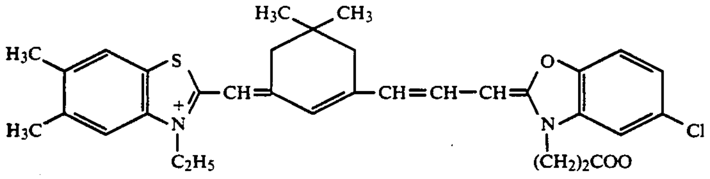
(II-8)
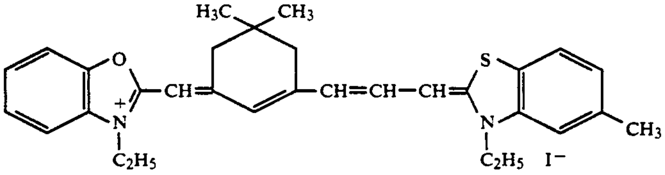
(II-9)
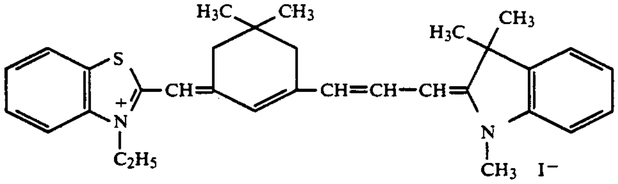
(II-10)
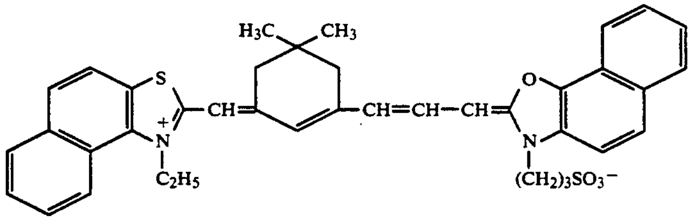
(II-11)
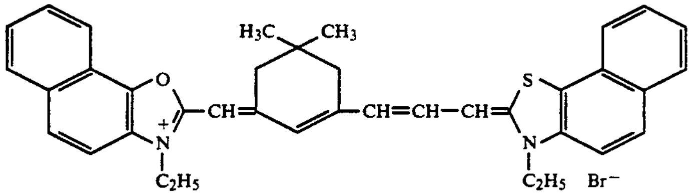
(II-12)

-continued
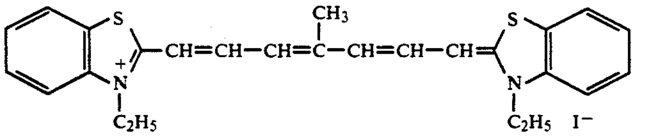
(II-13)
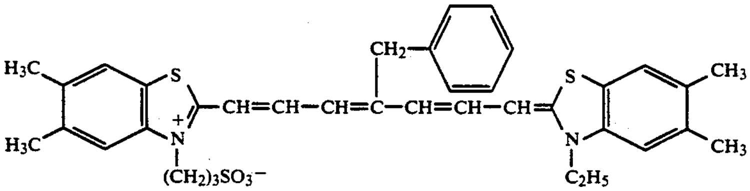
(II-14)
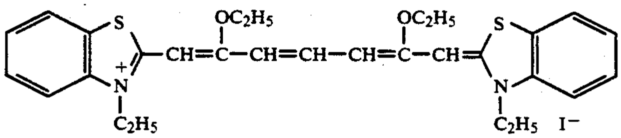
(II-15)
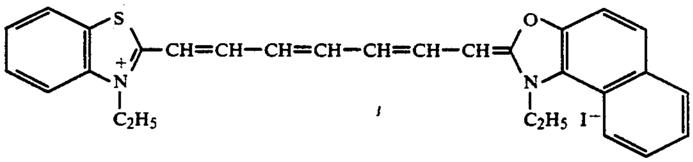
(II-16)
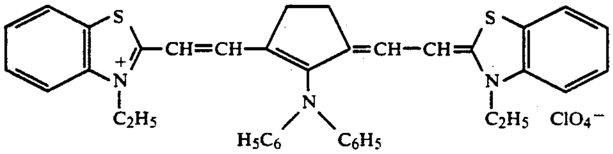
(II-17)
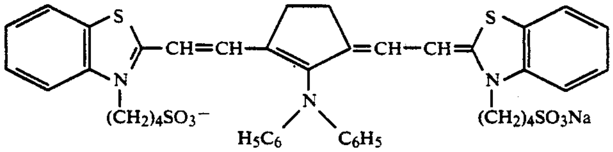
(II-18)
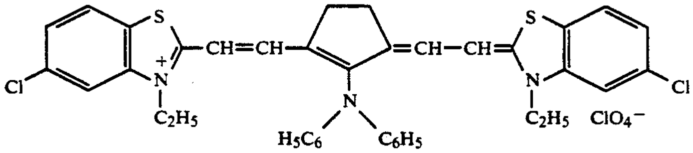
(II-19)
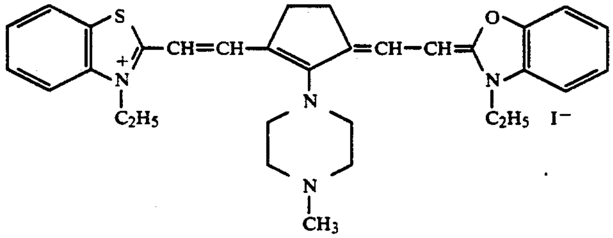
(II-20)
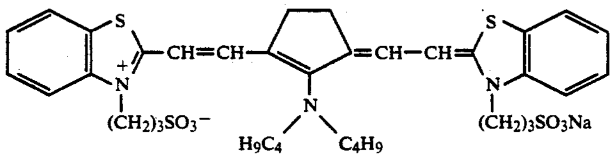
(II-21)

-continued
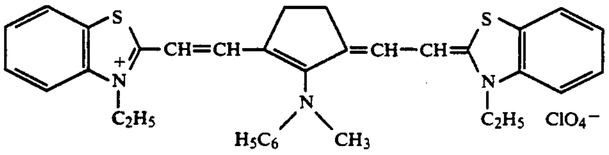
(II-22)
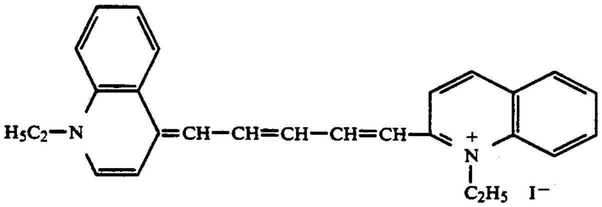
(II-23)
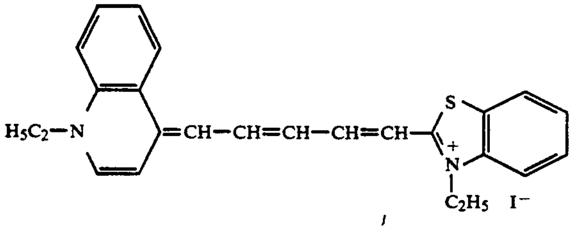
(II-24)
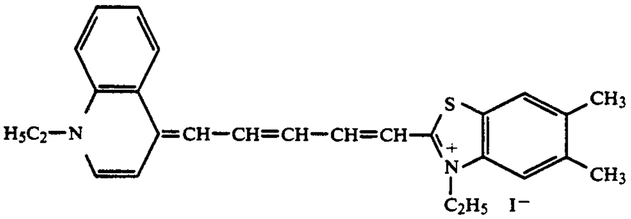
(II-25)
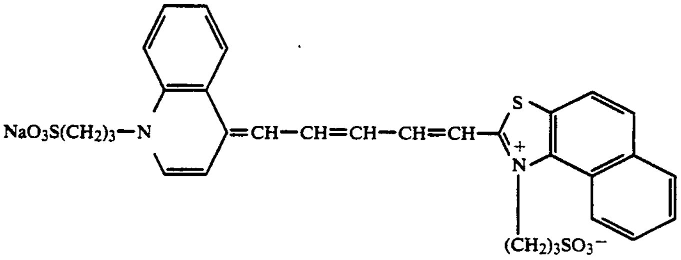
(II-26)
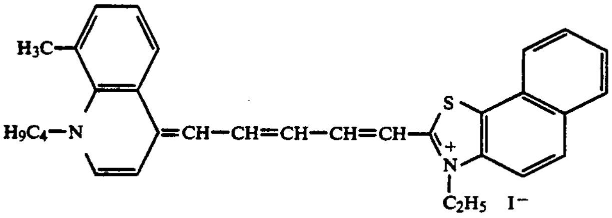
(II-27)
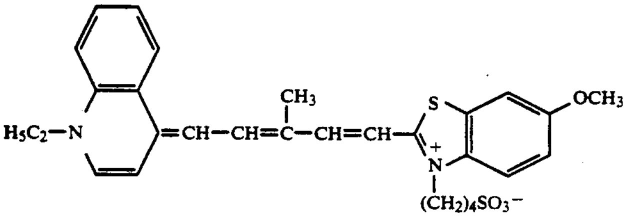
(II-28)

-continued
(II-29)
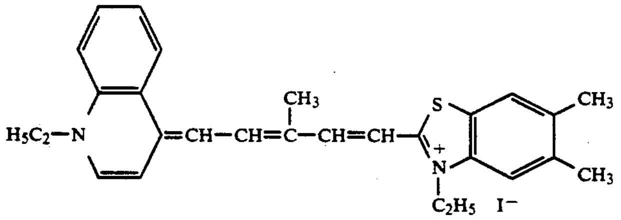
(II-30)
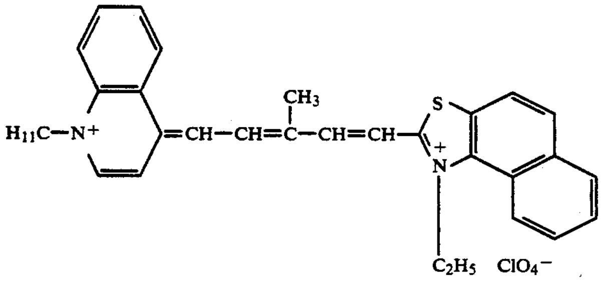
(II-31)
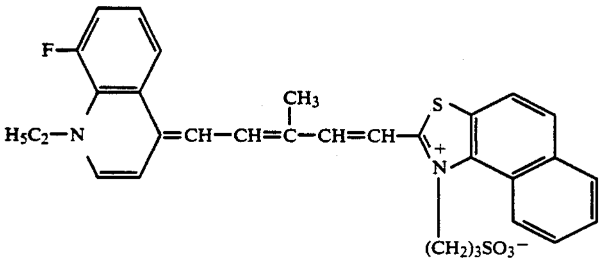
(II-32)
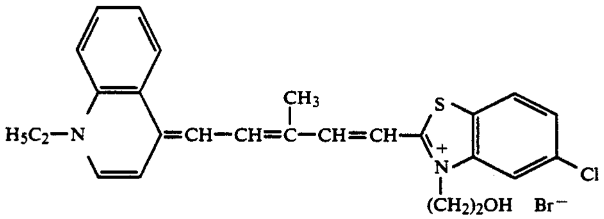
(II-33)
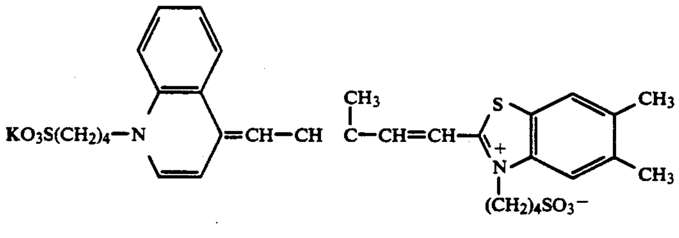
(II-34)
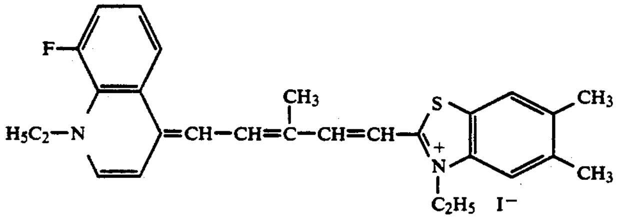

-continued
(II-35)
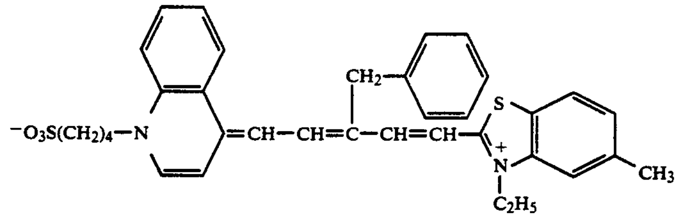
(II-36)
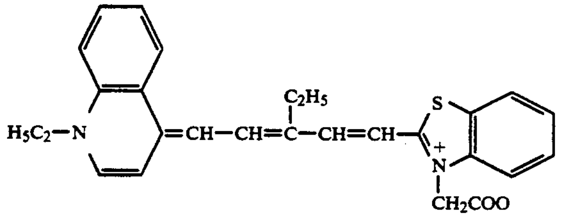
(II-37)
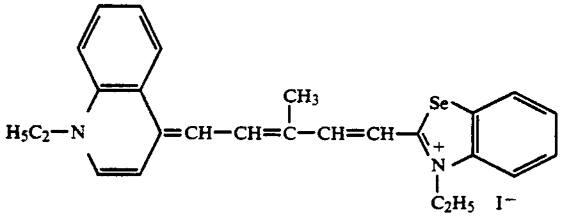
(II-38)
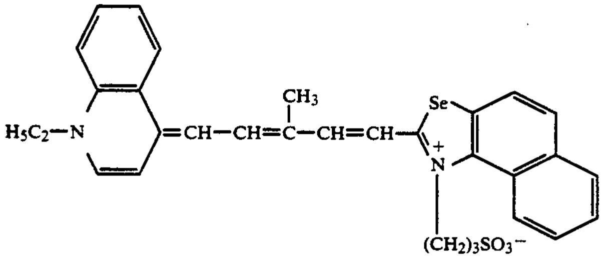
(II-39)
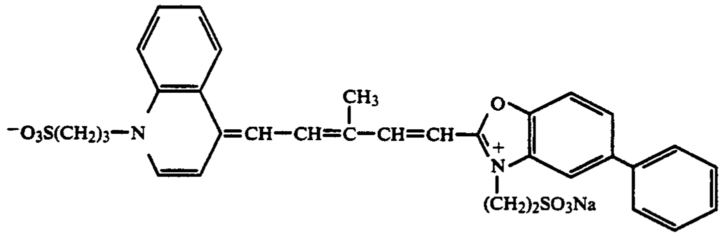
(II-40)
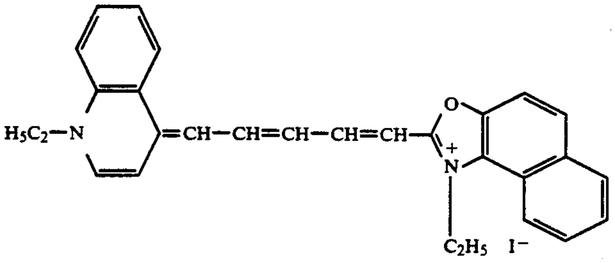

-continued (II-41)

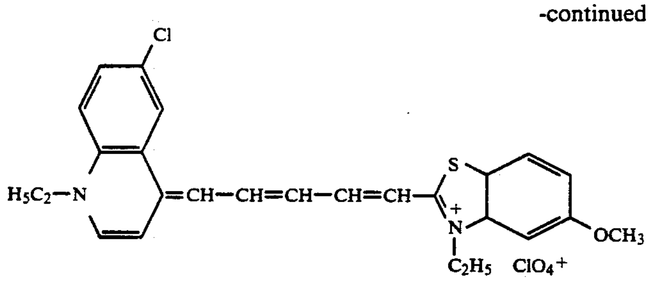

(II-42)

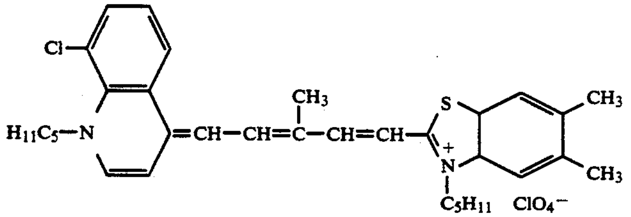

The above-mentioned infrared-sensitizing dye used in this invention can be contained in the silver halide photographic emulsion in an amount of $5\times10^{-7}$ to $5\times10^{-3}$ mol, preferably $1\times10^{-6}$ to $1\times10^{-3}$ mol, more preferably $2\times10^{-6}$ to $5\times10^{-4}$ mol, per mol of silver halide.

The above-mentioned infrared-sensitizing dye used in this invention may be dispersed directly into the emulsion layer. It may also be added to the emulsion in the form of solution in a proper solvent such as methyl alcohol, ethyl alcohol, methyl cellosolve, acetone, water, pyridine, and a mixture thereof. Ultrasonic may be used to effect dissolution. The above-mentioned infrared-sensitizing dye may be added in the following manners. (1) The dye is dissolved in a volatile organic solvent, the resulting solution is dispersed in a hydrophilic colloid, and the resulting dispersion is added to the emulsion (as described in U.S. Pat. No. 3,469,987). (2) The water insoluble dye is dispersed in a water-soluble solvent without dissolution, and the resulting dispersion is added to the emulsion (as described in Japanese Patent Publication No. 24185/1971). (3) The dye is dissolved in a surface active agent, and the resulting solution is added to the emulsion (as described in U.S. Pat. No. 3,822,135). (4) The dye is dissolved by the aid of a compound that brings about red-shifting, and the resulting solution is added to the emulsion (as described in Japanese Patent Application (OPI) No. 74624/1976). (5) The dye is dissolved in an acid containing substantially no water, and the resulting solution is added to the emulsion (as described in Japanese Patent Application (OPI) No. 80826/1975). Other adding methods are described in U.S. Pat. Nos. 2,912,343, 3,342,605, 2,996,287 and 3,429,835. The infrared-sensitizing dye represented by formula (II) may be uniformly dispersed in the silver halide emulsion prior to coating to the support. The dispersion may be carried out at any stage in the preparation of silver halide emulsion.

The sensitizing dye of this invention may be used in combination with other sensitizing dyes such as those described in U.S. Pat. Nos. 3,703,377, 2,688,545, 3,397,060, 3,615,635, 3,628,964, 3,416,927, 3,615,613, 3,615,632, 3,617,295, and 3,635,721; British Patent No. 1,242,588 and 1,293,862; and Japanese Patent Publication No. 4936/1968, 14030/1969, 10773/1968, and 4930/1968.

According to this invention, the compound represented by formula (III) below may be used to enhance supersensitization effect and/or to improve the shelf stability.

Formula (III):

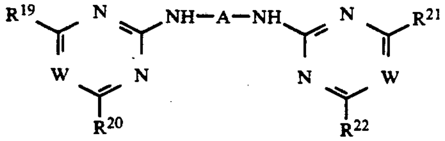

wherein —A— denotes a divalent aromatic residue which may contain a $—SO_3M$ group (where M denotes a hydrogen atom or a cation (e.g., sodium and potassium) that imparts the water solubility).

A preferred example of —A— is selected from $—A_1—$ or $—A_2—$ given below. When $R^{19}$, $R^{20}$, $R^{21}$, or $R^{22}$ does not contain $—SO_3M$, —A— is selected from the group of $—A_1—$.

$—A_1—$:

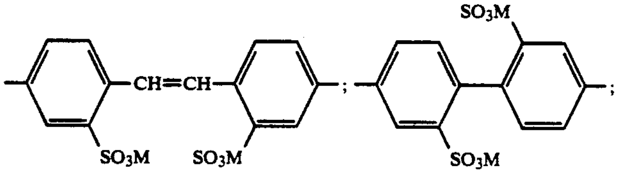

-continued

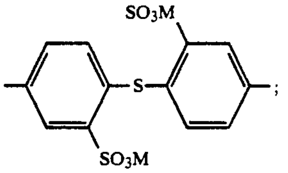
;

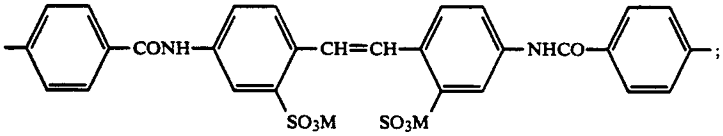
;

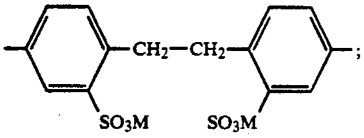
;
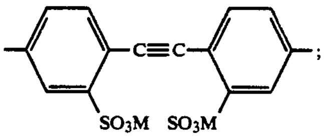
;

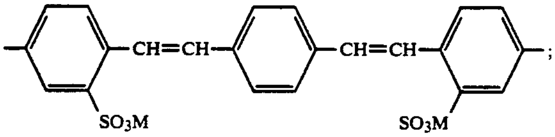
;

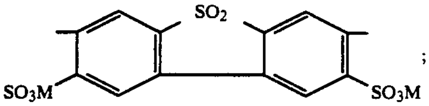
;

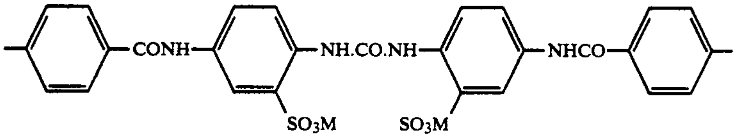

—$A_2$—:

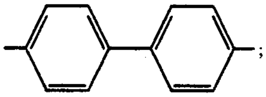
;
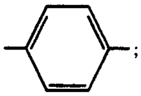
;

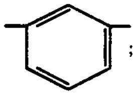
;
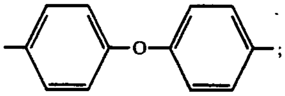
;

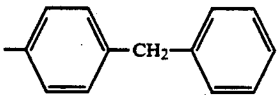
;
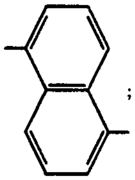
;

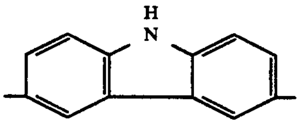

Wherein M represents a hydrogen atom or a cation that imparts the water solubility.

$R^{19}$, $R^{20}$, $R^{21}$, and $R^{22}$ each represents a hydrogen atom, hydroxyl group, lower alkyl group (preferably having 1 to 8 carbon atoms, e.g., methyl group, ethyl group, n-propyl group, and n-butyl group), alkoxy group (preferably having 1 to 8 carbon atoms, e.g., methoxy group, ethoxy group, propoxy group, and butoxy group), aryloxy group (e.g., phenoxy group, naphthoxy group, o-toloxy groups, and p-sulfophenoxy group), halogen atom (e.g., chlorine atom and bromine atom), heterocyclic ring nucleus (e.g., morpholinyl group and piperidyl group), alkylthio group (e.g., methylthio group and ethylthio group), heterocyclylthio group (e.g., benzothiazolylthio group, benzimidazolylthio group, and phenyltetrazolylthio group), arylthio group (e.g., phenylthio group and tolylthio group), amino group, alkylamino group or substituted alkylamino group (e.g., methylamino group, ethylamino group, propylamino group, dimethylamino group, diethylamino group, dodecylamino group, cyclohexylamino group, β-hydroxyethylamino group, di-(β-hydroxyethyl)amino group, and β-sulfoethylamino group), arylamino group or substituted arylamino group (e.g., anilino group, o-sulfoanilino group, m-sulfoanilino group, p-sulfoanilino group, o-toluidino group, m-toluidino group, p-toluidino group, o-carboxyanilino group, m-carboxyanilino group, p-carboxyanilino group, o-chloroanilino group, m-chloroanilino group, p-chloroanilino group, p-aminoanilino group, o-anisidino group, m-anisidino group, p-anisidino group, o-acetaminoanilino group, hydroxyanilino group, disulfophenylamino group, naphthylamino group, and sulfonaphthylamino group), heterocyclylamino group (e.g., 2-benzothiazolylamino group and 2-pyradyl-amino group), substituted or unsubstituted aralkylamino group (e.g., benzylamino group, o-anisylamino group, m-anisylamino group, and p-anisylamino group), aryl group (e.g., phenyl group), and mercapto group. $R^{19}$, $R^{20}$, $R^{21}$, and $R^{22}$ may be the same or different from one another. Where —A— is selected from the group of —$A_2$—, at least one of $R^{19}$, $R^{20}$, $R^{21}$, and $R^{22}$ should have one or more sulfo groups (in the form of free acid or salt). W denotes —CH= or —N=, the former being preferable.

The following are the examples of the compounds represented by formula (III) which are used in this invention. However, the scope of this invention is not limited to these compounds.

(III-1) Disodium salt of 4,4'-bis[4,6-di(benzothiazolyl-2-thio)pyrimidin-2-ylamino]stilbene-2,2'-disulfonic acid.

(III-2) Disodium salt of 4,4'-bis[4,6-di(benzothiazolyl-2-amino)pyrimidin-2-ylamino]stilbene-2,2'-disulfonic acid.

(III-3) Disodium salt of 4,4'-bis[4,6-di(naphthyl-2-oxy)-pyrimidin-2-ylamino]stilbene-2,2'-disulfonic acid.

(III-4) Disodium salt of 4,4'-bis[4,6-di(naphthyl-2-oxy)-pyrimidin-2-ylamino]dibenzyl-2,2'-disulfonic acid.

(III-5) Disodium salt of 4,4'-bis[4,6-dianilinopyrimidin-2-ylamino]stilbene-2,2'-disulfonic acid.

(III-6) Disodium salt of 4,4'-bis[4-chloro-6-(2-naphthyloxy)pyrimidin-2-ylamino]biphenyl-2,2'-disulfonic acid.

(III-7) Disodium salt of 4,4'-bis[4,6-di(1-phenyltetrazolyl-5-thio)pyrimidin-2-ylamino]stilbene-2,2'-disulfonic acid.

(III-8) Disodium salt of 4,4'-bis[4,6-di(benzoimidazolyl-2-thio)pyrimidin-2-ylamino]stilbene-2,2'-disulfonic acid.

(III-9) Disodium salt of 4,4'-bis(4,6-diphenoxypyrimidin-2-ylamino)stilbene-2,2'-disulfonic acid.

(III-10) Disodium salt of 4,4'-bis(4,6-diphenoxythiopyrimidin-2-ylamino)stilbene-2,2'-disulfonic acid.

(III-11) Disodium salt of 4,4'-bis(4,6-dimercaptopyrimidin-2-ylamino)biphenyl-2,2'-disulfonic acid.

(III-12) Disodium salt of 4,4'-bis(4,6-dianilinotriazin-2-ylamino)stilbene-2,2'-disulfonic acid.

(III-13) Disodium salt of 4,4'-bis(4-anilino-6-hydroxytriazin-2-ylamino)stilbene-2,2'-disulfonic acid.

(III-14) Disodium salt of 4,4'-bis(4-naphthylamino-6-anilinotriazin-2-ylamino)stilbene-2,2'-disulfonic acid.

Among the above-mentioned examples, (III-1) to (III-12) are preferable, and (III-1) to (III-5) and (III-7) are particularly preferable.

The compound of formula (III) is used in an amount of about 0.01 to 5 g per mol of silver halide in the emulsion.

The above-mentioned infrared-sensitizing dye of this invention and the compound represented by formula (III) is used in a ratio (by weight) of 1/1 to 1/100, preferably 1/2 to 1/50.

The compound represented by formula (III) is added in the same manner as the infrared sensitizer represented by formula (II).

According to this invention, the above-mentioned compounds may be used in combination with the compound represented by formula (IV) below.

Formula (IV):

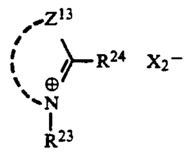

In formula (IV) $Z^{13}$ represents a group of non-metallic atoms necessary for the completion of a 5- or 6-membered nitrogen-containing heterocyclic ring, examples of which are given below. Thiazoliums (e.g., thiazolium, 4-methylthiazolium, benzothiazolium, 5-methylbenzothiazolium, 5-chlorobenzothiazolium, 5-methoxybenzothiazolium, 6-methoxybenzothiazolium, naphtho[1,2-d]thiazolium, and naphtho[2,1-d]thiazolium), oxazoliums (e.g., oxazolium, 4-methyloxazolium, benzoxazolium, 5-chlorobenzoxazolium, 5-phenylbenzoxazolium, 5-methylbenzoxazolium, and naphtho[1,2-d]oxazolium), imidazoliums (e.g., 1-methylbenzimidzolium, 1-propyl-5-chlorobenzimidazolium, 1-ethyl-5,6-dichlorobenzimidazolium, and 1-allyl-5-trichloromethyl-6-chloro-benzimidazolium). Selezoliums (e.g., benzoselinazolium, 5-chlorobenzoselenazolium, 5-methylbenzoselenazolium, 5-methoxybenzoselenazolium, and naphtho[1,2-d]selenazolium). $R^{23}$ represents a hydrogen atom, alkyl group (having 8 or less carbon atoms, e.g., methyl group, ethyl group, propyl group, butyl group, and pentyl group), and alkenyl group (e.g., allyl group). $R^{14}$ represents a hydrogen atom and lower alkyl group (e.g., methyl group and ethyl group). $X_2$ represents an acid anion (e.g., $Cl^-$, $Br^-$, $I^-$, $ClO_4^-$, and p-toluenesulfonic acid). $Z^{13}$ is preferably a thiazolium, and more preferably substituted or unsubstituted benzothiazolium or naphthothiazolium.

The following are the examples of the compound represented by formula (IV) but the scope of this invention is not limited to them.

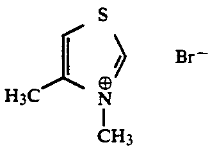
(IV-1)

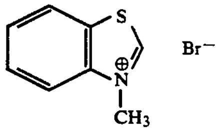
(IV-2)

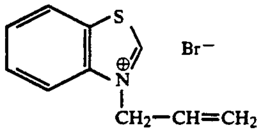
(IV-3)

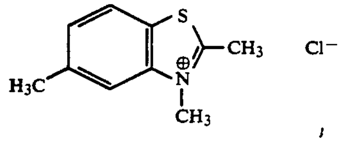
(IV-4)

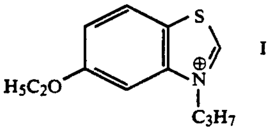
(IV-5)

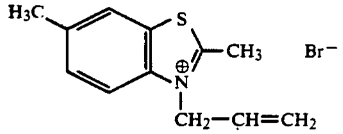
(IV-6)

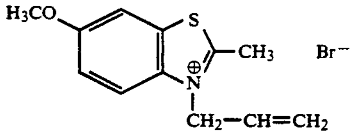
(IV-7)

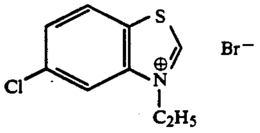
(IV-8)

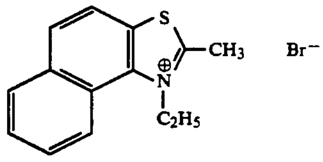
(IV-9)

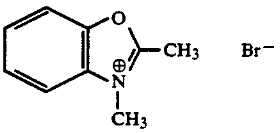
(IV-10)

-continued

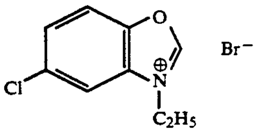
(IV-11)

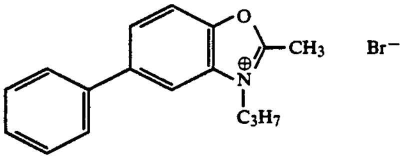
(IV-12)

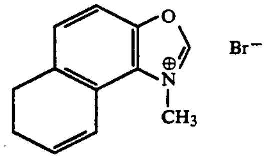
(IV-13)

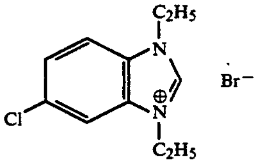
(IV-14)

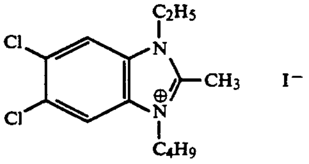
(IV-15)

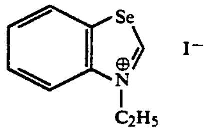
(IV-16)

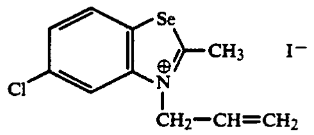
(IV-17)

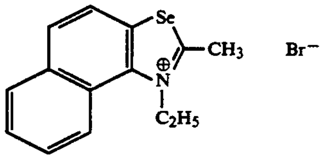
(IV-18)

The compound represented by the above formula (IV) is used in an amount of about 0.01 to 5 g per mol of silver halide in the emulsion.

The above-mentioned infrared-sensitizing dye represented by formula (II) and the compound represented by formula (IV) is used in a ratio (by weight) of 1/1 to 1/300, preferably 1/2 to 1/50.

The compound represented by formula (IV) is added in the same manner as the infrared sensitizer represented by formula (II).

The compound represented by formula (IV) may be added to the emulsion before or after the infrared-sensitizing dye of this invention is added. The compound of formula (IV) and the infrared-sensitizing dye may be dissolved separately and the resulting solutions may be added to the emulsion simultaneously but individually or after mixing.

The photographic emulsion used in this invention may contain a variety of compounds for the prevention of fog and decrease of sensitivity that would otherwise occur during the manufacturing process, preservation, or photographic processing. Examples of such compounds include nitrobenzimidazole, ammonium chloroplatinate, 4-hydroxy-6-methyl-1,3,3a,7-tetraazaindene, and 1-phenyl-5-mercaptotetrazole. Additional examples include heterocyclic compounds, mercury-containing compounds, mercapto compounds, and metal salts. Some examples of the compounds that can be used are listed with reference to the original literature in "The Theory of the Photographic Process", by K. Mees, 3rd ed. 1966, pp. 344–349.

The silver halide photosensitive material may contain a developing agent (e.g., hydroquinones, catechols, aminophenols, 3-pyrazolidones, ascorbic acid and derivatives thereof, reductones, and phenylenediamines), or a combination of developing agents.

Where the photosensitive material of this invention is used as a photosensitive material for printing, the silver halide emulsion may be incorporated with a polyalkylene oxide compound so that the photosensitive material has a characteristic curve with the toe of high contrast gradient so as to produce sharp dots and line images.

The polyalkylene oxide compound is a condensation product of a polyalkylene oxide and a compound having at least one active hydrogen, or a block copolymer composed of two or more kinds of polyalkylene oxides. (The polyalkylene oxide is composed of at least 10 units of alkylene oxides having 2 to 4 carbon atoms, for example, ethylene oxide, propylene-1,2-oxide, and butylene-1,2-oxide, with ethylene oxide being preferable. The compound containing at least one active hydrogen includes water, aliphatic alcohols, aromatic alcohols, fatty acids, organic amines, and hexitol derivatives.)

Examples of the polyalkylene oxide compounds include polyalkylene glycols, polyalkylene glycol alkyl ethers, polyalkylene glycol aryl ethers, polyalkylene glycol (alkylaryl) ethers, polyalkylene glycol esters, polyalkylene glycol fatty acid amides, polyalkylene glycol amines, polyalkylene glycol block copolymer, and polyalkylene glycol graft polymers. They should have a molecular weight higher than 600.

The polyalkylene oxide compound may contain two or more polyalkylene oxide chains in one molecule. In this case, individual polyalkylene oxide chains may be composed of less than 10 alkylene oxide units; but the total of alkylene oxide units in the molecule should be at least 10. When the molecule has two or more polyalkylene oxide chains, each of them may be composed of different kinds of alkylene oxides, e.g., ethylene oxide and propylene oxide. The polyalkylene oxide compound used in this invention should preferably contain 14 to 100 alkylene oxide units.

Typical examples of the polyalkylene oxide compound that can be used in this invention are described in Japanese Patent Application (OPI) Nos. 156423/1975, 108130/1977, and 3217/1978. These polyalkylene oxide compounds may be used individually or in combination with one another.

The polyalkylene oxide compound is dissolved in water or a water-miscible low-boiling organic solvent, and the resulting solution is added to the silver halide emulsion at a proper time prior to coating preferably after chemical ripening.

The polyalkylene oxide compound should be used in an amount of $1\times10^{-5}$ to $1\times10^{-2}$ mol per mol of silver halide.

The polyalkylene oxide compound may be added to a non-photosensitive hydrophilic colloid layer (e.g., intermediate layer, protective layer, and filter layer) instead of the silver halide emulsion.

Gelatin is advantageously used as a binder or protective colloid for the photosensitive material. A hydrophilic synthetic polymer can also be used. The gelatin that can be used is lime-treated gelatin, acid-treated gelatin, or gelatin derivatives.

The photosensitive material of this invention may be incorporated with, in addition to the above-mentioned additives, a variety of additives such as desensitizer, brightening agent, coupler, hardening agent, coating aid, plasticizer, antislip agent, matting agent, high-boiling organic solvent, stabilizer, development accelerator, antistatic agent, and stain inhibitor. Typical examples of the additives are described in Research Disclosure Vol. 176, No. 17643 (December 1978), Sections I to XIV (pp. 22–28).

The photosensitive material of this invention can be processed by a known method using known processing solutions. It may be processed by black and white photographic processing to form silver images or color photographic processing to form color images. The processing temperature is usually 18° C. to 50° C., although not limitative.

The black and white developing solution may contain known developing agents such as dihydroxybenzenes (e.g., hydroquinone), 3-pyrazolidones (e.g., 1-phenyl-3-pyrazolidone), and aminophenols (e.g., N-methyl-p-aminophenol) individually or in combination with one another (e.g., 1-phenyl-3-pyrazolidone and dihydroxybenzene, or p-aminophenol and dihydroxybenzene). The photosensitive material of this invention may be processed with a so-called infectious developing solution containing a sulfite ion buffer (e.g., carbonyl bisulfite) and hydroquinone. The developing solution should be adjusted to pH 9, preferably pH 9.7 and up.

The color developing solution is usually an alkaline solution containing a color developing agent. The color developing agent is a primary aromatic amine such as phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamido-ethylaniline, and 4-amino-3-methyl-N-ethyl-N-$\beta$-methoxyethylaniline).

Examples of other color developing agent that can be used are described in "Photographic Processing Chemistry", by L. F. A. Meson, issued by Focal Press (1966), pp. 226–229; U.S. Pat. Nos. 2,193,015 and 2,592,364; and Japanese Patent Application (OPI) No. 64933/1973.

The developing solution may contain a pH buffering agent (e.g., alkali metal sulfite, carbonate, borate, and phosphate) and a development retarder or antifoggant (e.g., bromide, iodide, polyalkylene oxide, and organic antifoggant. If necessary, it may also contain a water softener, preservative (e.g., hydroxylamine), organic solvent (e.g., benzyl alcohol and diethylene glycol), development accelerator (e.g., polyethylene glycol, quaternary ammonium salt, and amine), dye forming coupler, competitive coupler, fogging agent (e.g., sodium boron hydride), auxiliary developing agent (e.g., 1-phenyl-3-pyrazolidone), thickening agent, polycarboxylic acid-based chelating agent as described in U.S. Pat. No. 4,083,723, and antioxidant as described in West Germany Laid-open Patent (OLS) No. 2,622,950.

The developing solution may be incorporated with as a preservative a compound that gives free sulfite ions such as sodium sulfite, potassium sulfite, potassium metabisulfite, sodium bisulfite, and hydroxylamaine. The preservative for infectious development solutions may be formaldehyde sodium bisulfite which gives little sulfite ions.

For fixation of the photosensitive material of this invention, a conventional fixer can be used.

The fixing agent includes thiosulfates, thiocyanates, and organic sulfur compounds known to be effective as a fixing agent.

The fixer may contain a water-soluble aluminum salt as a hardening agent.

The fixer may also contain a complex of ethylenediaminetetraacetic acid and trivalent iron ion.

The silver halide photosensitive material of this invention may contain a nucleating agent such as hydrazine so that it is developed with a black and white developing solution of high pH, and fixed with a fixer containing a hardening agent.

The dye pertaining to the present invention has the absorption maximum at 730 to 850 nm. The silver halide photosensitive material containing this dye produces images of good quality when exposed to infrared rays and developed in the usual way. It has the advantage of producing little residual color after development without sacrificing the sensitivity to light in the infrared region. It has hydrophilic colloid layers which are colored with a water-soluble dye which has no adverse effect on the characteristics of the photographic emulsion and is readily discolored by the photographic processing.

To further illustrate this invention, and not by way of limitation, the following examples are given.

EXAMPLE 1

50 g of gelatin was dissolved in water. To this solution was added 3.1 g of dye shown in Table 1. To the solution were further added 30 ml of 4 wt % aqueous solution of sodium dodecylbenzenesulfonate as a surface active agent and 45 ml of 1 wt % aqueous solution of 1-hydroxy-3,5-dichlorotriazine sodium salt as a hardening agent. The resulting solution was adjusted to 1 liter. The gelatin-containing aqueous solution was coated on a cellulose treacetate film so as to form a dry coating having thickness of 5 μm.

The back side of the film opposite to the gelatin coating was coated with a silver halide emulsion having the following composition.

Silver halide: 1 kg of emulsion of silver chloroiodobromide (containing 70 mol % of bromine and 0.2 mol % of iodine, and having an average grain diameter of 0.45 μm), chemically sensitized with gold and sulfur compounds.

Sensitizing dye (II-1) as described in Japanese Patent Application (OPI) No. 192242/1984: 60 ml of 0.05 wt % methanol solution (The chemical name is given below.)

Compound (III-1) as described in Japanese Patent Application (OPI) No. 192242/1984: 40 ml of 1.0 wt % methanol solution (The chemical structure is given below.)

Sodium dodecylbenzenesulfonate: 30 ml of 4.0 wt % aqueous solution 1-Hydroxy-3,5-dichlorotriazine sodium salt: 35 ml of 1.0 wt % aqueous solution.

Then the emulsion layer was coated with an aqueous solution containing gelatin and sodium dodecylbenzenesulfonate to form a protective layer.

The photographic film thus formed was exposed to (A) infrared rays of 760 nm emitted by a light emitting diode or (B) infrared rays of 783 nm emitted by a semiconductor laser. The exposed film was developed at 38° C. for 20 seconds with a developing solution (LD-835, Tradename, merchandized by Fuji Photo Film Co., Ltd.) using an automatic developing machine FG-800RA (Tradename, merchandized by Fuji Photo Film Co., Ltd.).

The image quality was rated in five steps, ranging from "1" representing the very poor image quality with many fringes, to "5" representing the sharp image with no fringes. The residual color was rated in five steps, ranging from "1" representing a large amount of residual color, to "5" representing the complete absence of residual color.

The results are shown in Table 1.

Chemical name of II-1: Disodium salt of 4,4-bis[4,6-di(benzothiazolyl-2-thio)pyrimidin-2-ylamino]stilbene-2,2'-disulfonic acid.

Chemical structure of III-1:

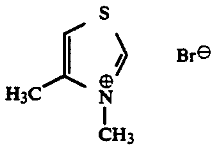

TABLE 1

| Sample No. | Dye No. | Image quality A | Image quality B | Residual color after processing |
|---|---|---|---|---|
| 1 (for comparison) | none | 1 | 1 | 5 |
| 2 | I-1 | 4 | 5 | 5 |
| 3 | I-8 | 4 | 5 | 5 |
| 4 | I-11 | 4 | 5 | 5 |
| 5 | I-13 | 4 | 5 | 5 |
| 6 | I-26 | 4 | 5 | 5 |
| 7 | I-29 | 4 | 5 | 5 |
| 8 (for comparison) | a* | 3 | 4 | 2 |

TABLE 1-continued

| Sample No. | Dye No. | Image quality A | Image quality B | Residual color after processing |
|---|---|---|---|---|
| 9 (for comparison) | b* | 3 | 4 | 3 |

Dye (a) for comparison is one having the following structure which is disclosed in British Patent No. 434,875.

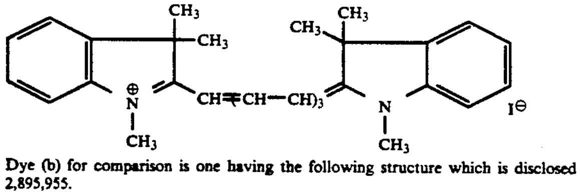

Dye (b) for comparison is one having the following structure which is disclosed in U.S. Pat. No. 2,895,955.

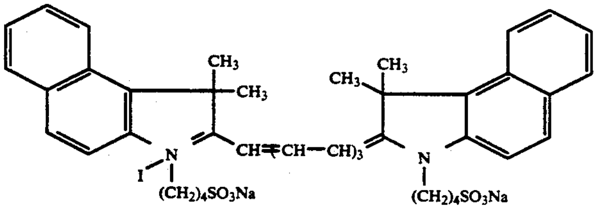

It is noted from Table 1 that the photographic film containing the dye of this invention formed an image of good quality and a minimum residual color, upon exposure to either a light emitting diode or a semiconductor laser.

EXAMPLE 2

50 g of gelatin was dissolved in 800 g of water. To this solution was added each dye as shown in Table 2. To the solution was further added a mordant dye in an amount of 1 $g/m^2$. (The chemical structure of the mordant dye is shown below.) The resulting solution was coated on a cellulose triacetate film. The gelatin layer was coated with an infrared-sensitized silver halide emulsion which is the same as the one in Example 1. Furthermore, the emulsion layer was coated with an aqueous solution containing gelatin and sodium dodecylbenzenesulfonate to form a protective layer.

The photographic film thus produced was exposed under an optical wedge through a dark red filter (SC-72 Tradename, made by Fuji Photo Film Co., Ltd.) The exposed film was developed at 20° C. for 4 minutes with the developing solution specified below, followed by stopping, fixing, and washing. The developed film was examined for density using a densitometer, Model P(Tradename), made by Fuji Photo Film Co., Ltd., whereby the sensitivity and fog level were determined. (Sensitivity is expressed in terms of the reciprocal of the amount of light that gives an optical density of fog plus 0.3.) The image quality was rated in the same manner as in Example 1.

| Formula of developing solution: | |
|---|---|
| Metol | 0.31 g |
| Anhydrous sodium sulfite | 39.6 g |
| Hydroquinone | 6.0 g |
| Anhydrous sodium carbonate | 18.7 g |
| Potassium bromide | 0.86 g |
| Citric acid | 0.68 g |
| Potassium metabisulfite | 1.5 g |
| Water to make 1 liter | |

Mordant dye A:

-continued

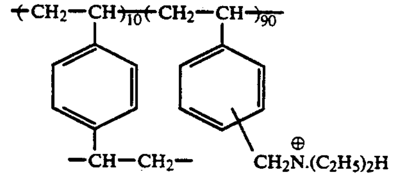

TABLE 2

| Film No. | Dye | Amount | Image quality Relative sensitivity | Image quality Fog | Image quality |
|---|---|---|---|---|---|
| 1 | — | — | 100** | 0.04 | 1 |
| 2 | I-3 | 0.01 $g/m^2$ | 74 | 0.04 | 3 |
| 3 | I-3 | 0.02 $g/m^2$ | 63 | 0.04 | 4 |
| 4 | I-11 | 0.01 $g/m^2$ | 91 | 0.04 | 3 |
| 5 | I-11 | 0.02 $g/m^2$ | 79 | 0.04 | 4 |
| 6 | I-27 | 0.01 $g/m^2$ | 93 | 0.04 | 3 |
| 7 | I-27 | 0.02 $g/m^2$ | 87 | 0.04 | 4 |
| 8 | I-30 | 0.01 $g/m^2$ | 91 | 0.04 | 3 |
| 9 | I-30 | 0.02 $g/m^2$ | 81 | 0.04 | 4 |
| 10* | a | 0.02 $g/m^2$ | 33 | 0.10 | 1 |
| 11* | b | 0.02 $g/m^2$ | 42 | 0.09 | 2 |

*For comparison
**Reference Dye "a" and dye "b" are the same as those in Example 1.

It is noted from Table 2 that the dye of this invention slightly decreases the sensitivity, but the extent of decrease is by far smaller than that in the case of comparative dyes. In addition, the dye of this invention provides good image quality and reduces the fog (see film Nos. 2-9).

EXAMPLE 3

The films obtained in Example 2 were exposed to infrared rays of 783 nm emitted by a semiconductor laser. The exposed films were developed at 38° C. for 30 seconds with a developing solution for printing (GS-1(Tradename), made by Fuji Photo Film Co., Ltd.).

The image quality was rated in the same manner as in Example 1. The results are shown in Table 3.

TABLE 3

| Film No. | Fog | Image quality |
|---|---|---|
| 1 | 0.04 | 1 |
| 2 | 0.04 | 4 |
| 3 | 0.04 | 5 |
| 4 | 0.04 | 4 |
| 5 | 0.04 | 5 |
| 6 | 0.04 | 4 |
| 7 | 0.04 | 5 |
| 8 | 0.04 | 4 |
| 9 | 0.04 | 5 |
| 10* | 0.10 | 1 |
| 11* | 0.09 | 2 |

*For comparison

It is noted from Table 3 that the photosensitive materials of this invention produce images of good quality and remarkably reduces the fog.

EXAMPLE 4

A cellulose triacetate film was coated with a silver halide emulsion of the following composition.

Silver halide: 1 kg of emulsion of silver chlorobromide (containing 80 mol % of bromine, and having an average grain diameter of 0.32 μm) chemically sensitized with gold and sulfur compounds.

Sensitizing dye (II-1): 70 ml of 0.05 wt % methanol solution (The same one as in Example 1)

Compound (III-1): 40 ml of 1.0 wt % methanol solution (The same one as in Example 1)

Dye: as shown in Table 4.

Sodium dodecylbenzenesulfonate: 35 ml of 4.0 wt % aqueous solution.

The emulsion layer was coated with an aqueous solution containing gelatin and sodium dodecylbenzenesulfonate to form a protective layer.

The photographic film thus produced was exposed to infrared rays of 783 nm emitted by a semiconductor laser. The exposed film was developed according to the super HSL system (Tradename, made by Fuji Photo Film Co., Ltd.)

The image quality was rated in five steps, ranging from "1" representing the very poor image quality with many fringes, to "5" representing the sharp image with no fringes. The residual color was rated in five steps, "1" representing a large amount of residual color, and "5" representing the complete absence of residual color.

The results are shown in Table 4.

TABLE 4

| Sample No. | Dye No. | Image quality | Residual color | Relative sensitivity | Fog |
|---|---|---|---|---|---|
| 1 | — | 1 | 5 | 100 | 0.04 |
| 2 | I-1 (70 mg) | 4 | 5 | 69 | 0.04 |
| 3 | I-7 (80 mg) | 4 | 5 | 71 | 0.04 |
| 4 | I-9 (70 mg) | 4 | 5 | 74 | 0.04 |
| 5 | a (70 mg) | 3 | 2 | 59 | 0.06 |
| 6 | b (70 mg) | 3 | 3 | 63 | 0.06 |

Dyes "a" and "b" for comparison are the same as those in Example 1.

It is noted from Table 4 that the dye of this invention provides images of good quality and reduces the residual color, showing a minimum of decrease in sensitivity, and being low in fog.

What is claimed is:

1. A dye represented by formula (I):

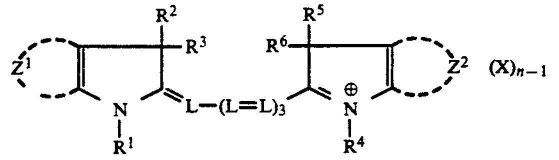

wherein $R^1$, $R^2$, $R^3$, $R^4$, $R^5$ and $R^6$, which may be the same or different, each represents a $C_1$-$C_5$ alkyl group or a $C_1$-$C_5$ alkyl group having a substituent selected from the group consisting of a sulfonic group, carboxyl group and hydroxyl group, and $Z^1$ and $Z^2$ each represents a group of non-metallic atoms necessary for the formation of a benzo-condensed or naphtho-condensed ring, or a benzo-condensed or naphtho-condensed ring having a substituent selected from the group consisting of a sulfonic group, a carboxyl group, an hydroxyl group, a halogen atom, a cyano group, an amino group and a $C_1$-$C_5$ alkyl group connected to the ring directly or through a divalent connection group, with a proviso that $R^1$, $R^2$, $R^3$, $R^4$, $R^5$, $R^6$, $Z^1$ and $Z^2$ represent those groups which permit the dye molecule to have at least three acid radicals; L represents a methine group or a methine group having a substituent selected from the group consisting of a $C_1$-$C_5$ alkyl group, a $C_1$-$C_5$ alkyl group having a substituent selected from an hydroxyl group, a phenyl group, and a sulfo group, a halogen atom, a phenyl group, a 4-chlorophenyl group, and a $C_1$-$C_2$ alkoxyl group; X represents an anion; and n represents 1 or 2, n being 1 when the dye forms an inner salt.

2. The dye as claimed in claim 1, wherein $R^1$, $R^2$, $R^3$, $R^4$, $R^5$ and $R^6$ each represents an alkyl group containing 1 to 5 carbon atoms.

3. The dye as claimed in claim 1, wherein each $R^1$ and $R^4$ represents an alkyl group containing 1 to 5 carbon atoms and having a sulfonic group.

4. The dye as claimed in claim 1, wherein the acid radical as a substituent of $R^1$, $R^2$, $R^3$, $R^4$, $R^5$, $R^6$ and $Z^1$ and $Z^2$ is selected from the group consisting of a sulfonic group and carboxylic group.

5. The dye as claimed in claim 1, wherein $R^1$, $R^2$, $R^3$, $R^4$, $R^5$, $R^6$, $Z^1$ and $Z^2$ have 4 to 6 sulfonic groups.

6. The dye as claimed in claim 1, wherein L represents an unsubstituted methine group.

7. The dye as claimed in claim 1, wherein the methine group represented by L has a $C_1$-$C_5$ alkyl group as a substituent.

8. The dye as claimed in claim 1, wherein the amino group has a substituent selected from the group consisting of $C_1$-$C_4$ alkyl groups.

9. The dye as claimed in claim 1, wherein the divalent connecting group is selected from the group consisting of —O—, —NHCO—, $—NHSO_2—$, —NHCOO—, —NHCONH—, —COO—, —CO—, and $—SO_2—$.

10. The dye as claimed in claim 1, wherein $R^1$ and $R^4$ are $C_1$-$C_5$ alkyl groups having a sulfonic acid group selected from the group consisting of a 2-sulfoethyl group, a 3-sulfopropyl group, and a 4-sulfobutyl group.

11. The dye as claimed in claim 1, wherein the halogen atom is selected from the group consisting fluorine, chlorine and bromine.

12. The dye as claimed in claim 1, wherein the amino group is selected from the group consisting of a dimethylamino group, a diethylamino group, an ethyl-4-sulfobutylamino group, and a di(3-sulfopropyl)amino group.

* * * * *